United States Patent
Calle et al.

(10) Patent No.: US 10,589,094 B2
(45) Date of Patent: Mar. 17, 2020

(54) SYSTEMS AND METHODS FOR CREATING AND USING SOUND PROCESSING PROGRAM TEMPLATES

(71) Applicant: ADVANCED BIONICS AG, Staefa (CH)

(72) Inventors: Guillermo A. Calle, Moorpark, CA (US); Gulamali Emadi, Van Nuys, CA (US); Steve Siefken, Castaic, CA (US)

(73) Assignee: Advanced Bionics AG, Staefa (CH)

(*) Notice: Subject to any disclaimer, the term of this patent is extended or adjusted under 35 U.S.C. 154(b) by 89 days.

(21) Appl. No.: 15/563,500

(22) PCT Filed: Apr. 30, 2015

(86) PCT No.: PCT/US2015/028614
§ 371 (c)(1),
(2) Date: Sep. 29, 2017

(87) PCT Pub. No.: WO2016/175854
PCT Pub. Date: Nov. 3, 2016

(65) Prior Publication Data
US 2018/0085582 A1    Mar. 29, 2018

(51) Int. Cl.
*G06F 3/0482* (2013.01)
*A61N 1/36* (2006.01)
(Continued)

(52) U.S. Cl.
CPC ..... *A61N 1/36038* (2017.08); *A61N 1/36036* (2017.08); *A61N 1/37217* (2013.01);
(Continued)

(58) Field of Classification Search
CPC ............ G06F 15/0283; G06F 9/44505; G06F 3/0482; G06F 3/04847; G06F 3/165;
(Continued)

(56) References Cited

U.S. PATENT DOCUMENTS 6,289,247 B1 *  9/2001  Faltys ................ A61N 1/36036
                                                      607/55
7,814,089 B1 * 10/2010  Skrenta ................. G06F 16/951
                                                      707/709
(Continued)

OTHER PUBLICATIONS

International Search Report and Written Opinion received in International Application No. PCT/US15/028614, dated Jan. 15, 2016.

*Primary Examiner* — Wilson W Tsui
(74) *Attorney, Agent, or Firm* — ALG Intellectual Property, LLC

(57) ABSTRACT

An exemplary programming system 1) detects a first input command representative of a request to create a sound processing program, 2) provides, in response to the first input command, a user interface that shows a plurality of default values corresponding to a plurality of parameters associated with the sound processing program, 3) detects a changing, by way of the user interface, of the plurality of default values to a plurality of modified values, 4) detects, subsequent to the changing, a second input command representative of a request to create a sound processing program template configured to serve as a basis for one or more additional sound processing programs, and 5) presents, in response to the second input command, an option that allows the user to select one or more of the modified values to be included in the sound processing program template.

20 Claims, 13 Drawing Sheets

(51) Int. Cl.
  *H04R 25/00* (2006.01)
  *A61N 1/372* (2006.01)
  *G06F 3/0484* (2013.01)
  *G06F 3/16* (2006.01)

(52) U.S. Cl.
  CPC ..... *A61N 1/37247* (2013.01); *A61N 1/37264* (2013.01); *G06F 3/0482* (2013.01); *G06F 3/04847* (2013.01); *G06F 3/165* (2013.01); *H04R 25/70* (2013.01); *H04R 25/606* (2013.01); *H04R 2225/55* (2013.01); *H04R 2225/67* (2013.01)

(58) Field of Classification Search
  CPC .............. A61N 1/36036; A61N 1/0541; A61N 1/37241; A61N 1/37264; A61N 1/37288; H04R 25/70; H04R 2225/41; H04R 2225/43; H04R 2225/55; H04R 2225/61; H04R 25/30; H04R 25/353; H04R 25/50; H04R 25/552
  See application file for complete search history.

(56) References Cited

U.S. PATENT DOCUMENTS

| | | | |
|---|---|---|---|
| 8,583,244 B1 | 11/2013 | Calle et al. | |
| 8,583,245 B1 | 11/2013 | Johnston et al. | |
| 9,613,028 B2* | 4/2017 | Foo | H04R 25/50 |
| 2003/0055355 A1* | 3/2003 | Viertio-Oja | A61B 5/0476 |
| | | | 600/544 |
| 2005/0076002 A1* | 4/2005 | Williams | G06F 9/44505 |
| 2011/0047162 A1* | 2/2011 | Brindisi | G06F 15/0283 |
| | | | 707/740 |
| 2011/0060384 A1* | 3/2011 | Lineaweaver | A61N 1/37247 |
| | | | 607/57 |
| 2012/0029593 A1 | 2/2012 | Calle et al. | |
| 2012/0134521 A1 | 5/2012 | Wessel et al. | |
| 2012/0219159 A1 | 8/2012 | Burk et al. | |
| 2013/0013027 A1* | 1/2013 | Lievens | A61N 1/37247 |
| | | | 607/57 |
| 2013/0205131 A1* | 8/2013 | Lee | H04M 1/72522 |
| | | | 713/100 |

* cited by examiner

SYSTEMS AND METHODS FOR CREATING AND USING SOUND PROCESSING PROGRAM TEMPLATES

BACKGROUND INFORMATION

In order to customize how a sound processor included in a cochlear implant system operates, an audiologist may utilize a programming system to create a sound processing program and then load the sound processing program onto the sound processor. Some sound processing programs may specify how the sound processor is to process audio content and/or direct a cochlear implant included in the cochlear implant system to generate and apply electrical stimulation representative of the audio content. Other sound processing programs may be configured to facilitate measurement by the sound processor of one or more electrode impedances, performance by the sound processor of one or more neural response detection operations, and/or performance by the sound processor of one or more diagnostics procedures associated with the cochlear implant system.

Creation of a sound processing program typically involves specifying specific values for a number of different parameters associated with the sound processing program. For example, an audiologist may utilize a graphical user interface displayed by a programming system to manually adjust one or more most comfortable loudness levels ("M levels"), threshold levels ("T levels"), volume levels, sensitivity levels, and a plethora of other parameters associated with a particular sound processing program. Specifying values for so many parameters is often a time consuming and laborious task for the audiologist and patient alike.

Even though the optimal values for many parameters associated with a sound processing program are patient-specific and require patient feedback in order to properly identify, an audiologist often knows, based on prior experience with other patients, that some optimal values are going to be within a certain range. For example, if the patient is a child, the audiologist may assume that the optimal values for some parameters are going to be similar to optimal values that the audiologist has seen in other pediatric patients. Hence, when creating a sound processing program for the child, the audiologist may first adjust values for these parameters to be at or near what the audiologist believes the optimal values may be. The audiologist may then make incremental changes to the values, e.g., based on patient feedback, in order to determine what the actual optimal values really are.

Unfortunately, conventional programming systems require an audiologist to make this initial adjustment of values each time a new sound processing program is created. This is because the values always start out being equal to the same default values each time a new sound processing program is created.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
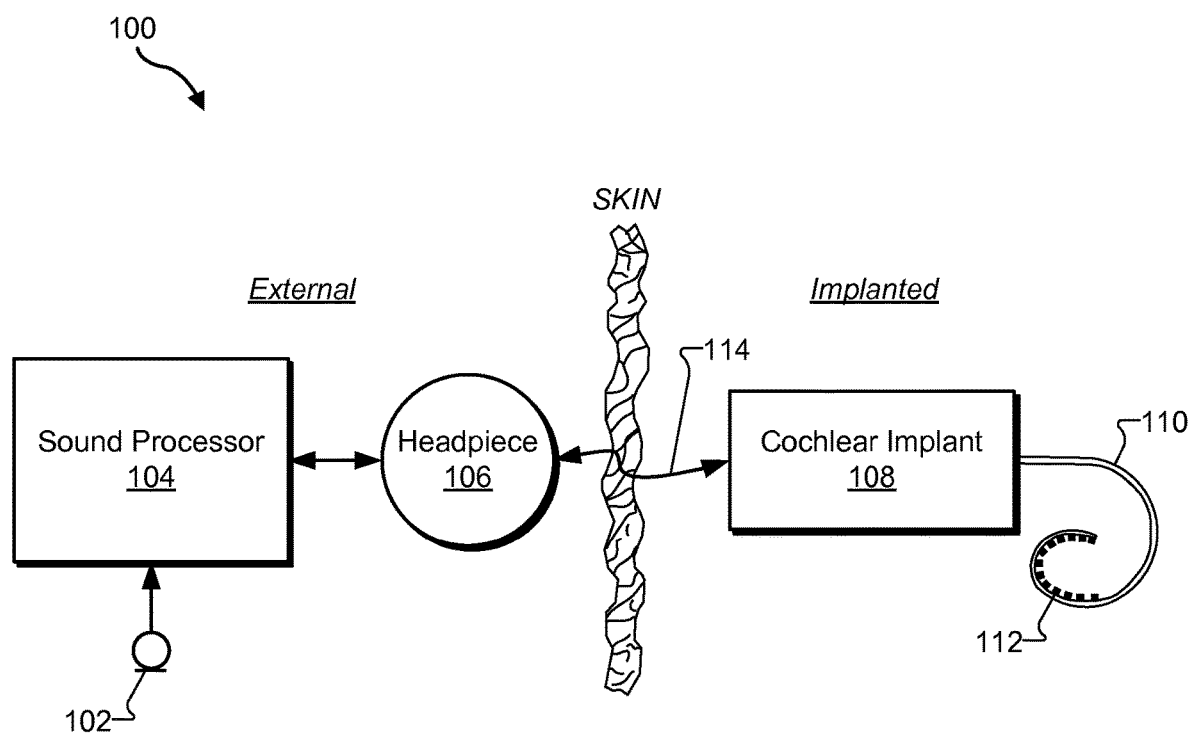
FIG. 1 illustrates an exemplary cochlear implant system according to principles described herein.

Systems and methods for creating sound processing program templates and using the sound processing program templates to generate sound processing programs for a cochlear implant system are described herein. As will be described below, a programming system may detect a first input command provided by a user and representative of a request to create a sound processing program for a cochlear implant system. In response to the first input command, the programming system may provide a user interface that shows a plurality of default values corresponding to a plurality of parameters associated with the sound processing program. The programming system may detect a changing, by the user by way of the user interface, of the plurality of default values corresponding to the plurality of parameters to a plurality of modified values corresponding to the plurality of parameters. Subsequently, the programming system may detect a second input command provided by the user and representative of a request to create a sound processing program template configured to serve as a basis for one or more additional sound processing programs. In response to the second input command, the programming system may present an option that allows the user to select one or more of the modified values to be included in the sound processing program template.

Once the user has selected the one or more modified values for inclusion in the sound processing program, the programming system may create the sound processing program template by including the one or more modified values in the sound processing program template. For parameters that have modified values that the user did not select for inclusion, the programming system may include default values in the sound processing program template. In this manner, the user may selectively include some modified values to the exclusion of other modified values in the sound processing program template.

Once the sound processing program template is created, the programming system may use the sound processing program template as a basis for creating subsequent sound processing programs. For example, subsequent to the sound processing program template being created, a user of the programming system may provide an input command representative of a request to create a new sound processing program. In response, the programming system may provide another user interface that shows a plurality of default values corresponding to a plurality of parameters associated with the new sound processing program. From this user interface, the user may select an option to apply the sound processing program template to the new sound processing program. In response to the selection of the option, the programming system may apply the sound processing program template to the new sound processing program by overwriting one or more of the values included in the new sound processing program with one or more of the modified values included in the sound processing program template.

By facilitating creation of a sound processing program template, the systems and methods described herein may allow a user (e.g., an audiologist) to more efficiently, accurately, and effectively generate a sound processing program for a particular cochlear implant patient. Moreover, the systems and methods described herein may allow the user to selectively include modified values corresponding to specific parameters (to the exclusion of modified values for other parameters) in the sound processing program, thereby allowing the user to create a highly customizable sound processing program template. When creating a new sound processing program based on a sound processing program template generated in accordance with the systems and methods described herein, the systems and methods described herein may allow a user to selectively apply some of the modified values included in the sound processing program template to the new sound processing program (and not apply the other modified values included in the sound processing program template). In this manner, the user may use a particular sound processing program template to create a new sound processing program, even though the user may not want to use all of the default values in the sound processing program template for the sound processing program.

As used herein, a "sound processing program" may specify how a sound processor included in a cochlear implant system is to process audio content and/or direct a cochlear implant included in the cochlear implant system to generate and apply electrical stimulation representative of the audio content. A sound processing program may additionally or alternatively specify one or more settings utilized by the cochlear implant system while the cochlear implant system performs one or more neural response imaging ("NRI") measurements, measures one or more electrode impedances, and/or performs one or more diagnostics procedures.

FIG. 1 illustrates an exemplary cochlear implant system 100. As shown, cochlear implant system 100 may include various components configured to be located external to a user including, but not limited to, a microphone 102, a sound processor 104, and a headpiece 106. Cochlear implant system 100 may further include various components configured to be implanted within the user including, but not limited to, a cochlear implant 108 and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the user. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a user.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bidirectional communication link and/or one or more dedicated unidirectional communication links. In some examples, sound processor 104 may execute and operate in accordance with a sound processing program that has been loaded into memory contained within sound processor 104.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the user's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bidirectional communication link and/or one or more dedicated unidirectional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a user and configured to apply stimulation to one or more stimulation sites located along an auditory pathway of a user.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the user via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
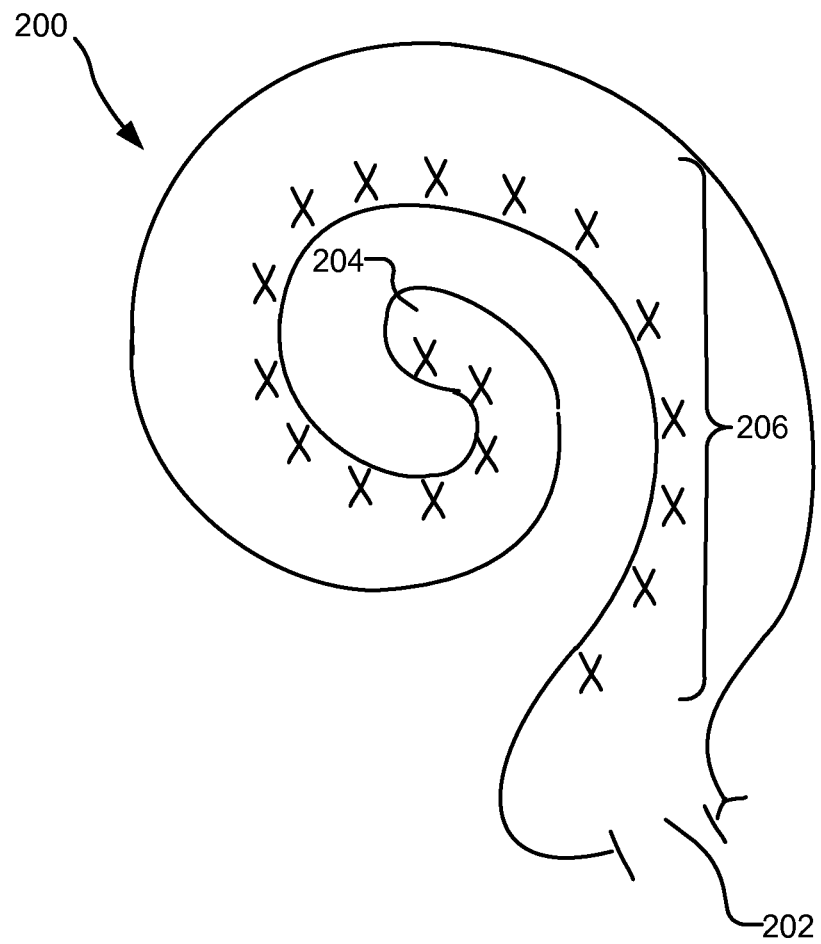
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

In some examples, a programming system separate from (i.e., not included within) cochlear implant system 100 may be selectively coupled to sound processor 104 in order to perform one or more fitting operations with respect to cochlear implant system 100, create and load one or more sound processing programs onto sound processor 104, and/or otherwise configure sound processor 104 as may serve a particular implementation.

Figure 3:
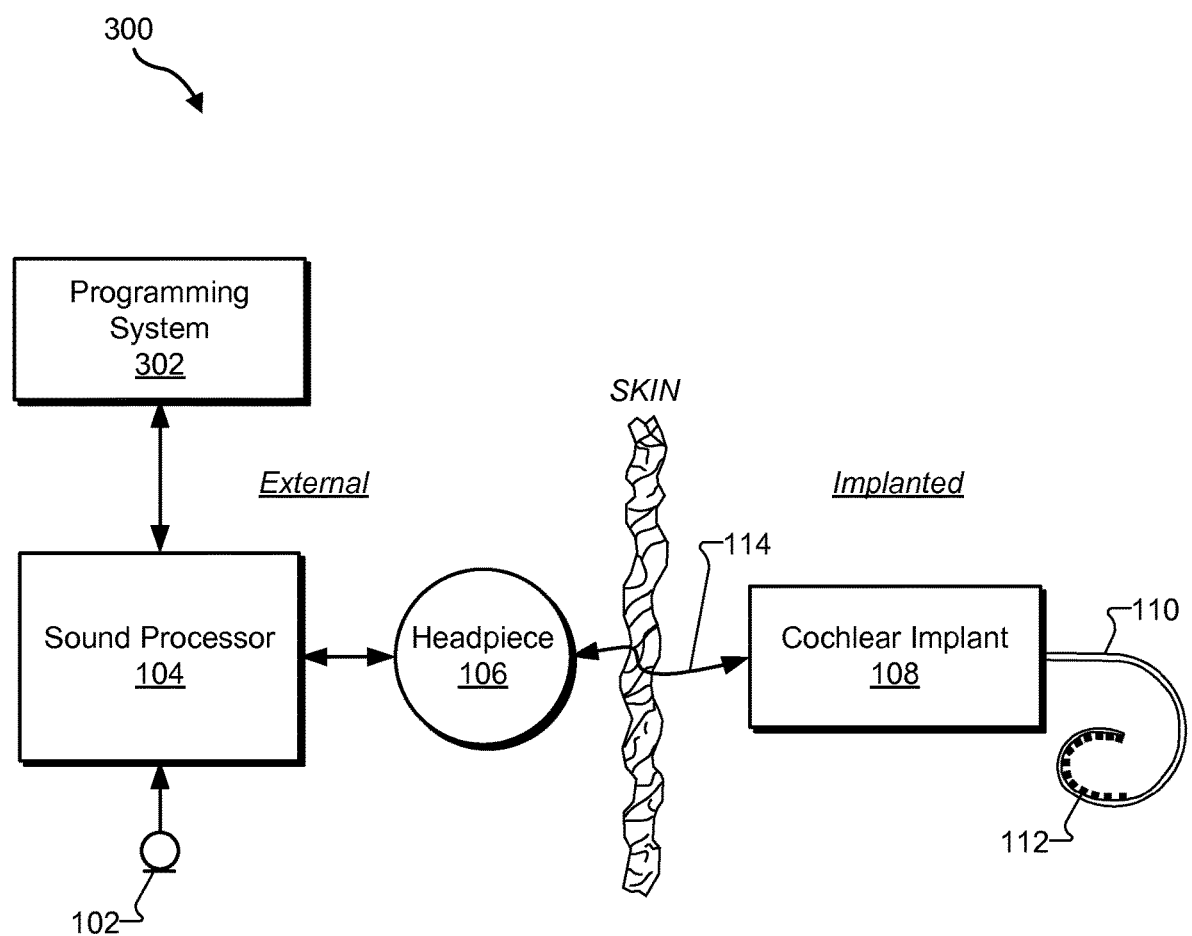
FIG. 3 shows an exemplary configuration in which a programming system is communicatively coupled to a sound processor according to principles described herein.

To illustrate, FIG. 3 shows an exemplary configuration 300 in which a programming system 302 is communicatively coupled to sound processor 104. Programming system 302 may be implemented by any suitable combination of computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation. In some examples, programming system 302 may provide one or more graphical user interfaces ("GUIs") (e.g., by presenting the one or more GUIs by way of a display screen) with which a clinician or other user may interact.

In some examples, programming system 302 may be implemented by a fitting device configured to generate sound processing programs that may be loaded on to sound processor 104 for execution by sound processor 104. To this end, programming system 302 may be configured to receive user input commands (e.g., by way of a keyboard and/or other user input device). Programming system 302 may transmit data representative of sound processing programs and/or any other information to sound processor 104 in any suitable manner.

Figure 4:
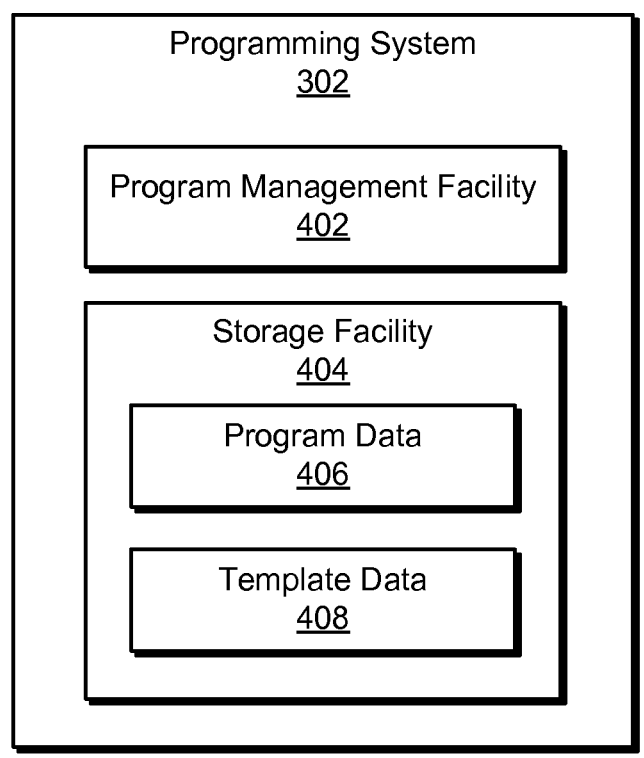
FIG. 4 illustrates an exemplary programming system according to principles described herein.

FIG. 4 illustrates exemplary components of programming system 302. As shown, programming system 302 may include a program management facility 402 ("management facility 402") and a storage facility 404, which may be in communication with one another using any suitable communication technologies. Storage facility 404 may maintain program data 406 representative of one or more sound processing programs and template data 408 representative of one or more sound processing program templates. Storage facility 404 may maintain additional or alternative data as may serve a particular implementation.

Management facility 402 may perform various program management operations. For example, management facility 402 may create a sound processing program template. Management facility 402 may use the sound processing program to create a sound processing program and then load the sound processing program onto a sound processor (e.g., sound processor 104) so that the sound processor may execute and operate in accordance with the sound processing program. Each of these operations will be described in more detail below.

Figure 5:
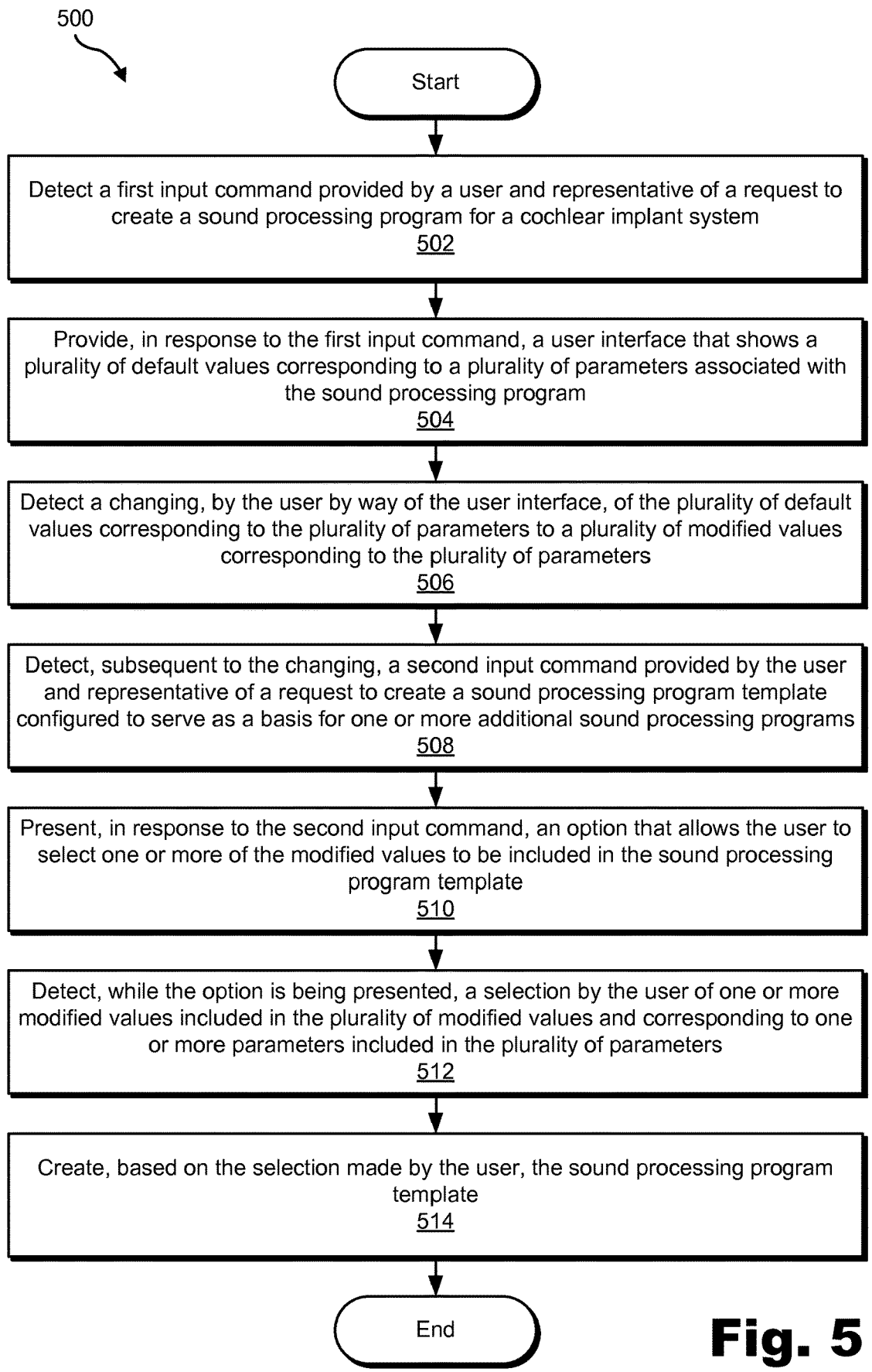
FIG. 5 illustrates an exemplary method of creating a sound processing program template according to principles described herein.

FIG. 5 illustrates an exemplary method 500 of creating a sound processing program template. While FIG. 5 illustrates exemplary steps according to one embodiment, other embodiments may omit, add to, reorder, and/or modify any of the steps shown in FIG. 5. One or more of the steps shown in FIG. 5 may be performed by programming system 302 (e.g., management facility 402) and/or any implementation thereof.

In step 502, programming system 302 detects a first input command provided by a user and representative of a request to create a sound processing program for a cochlear implant system. Step 502 may be performed in any suitable manner. For example, programming system 302 may detect the first input command by detecting a selection by the user of an option presented within a user interface to create a new sound processing program.

Figure 6:
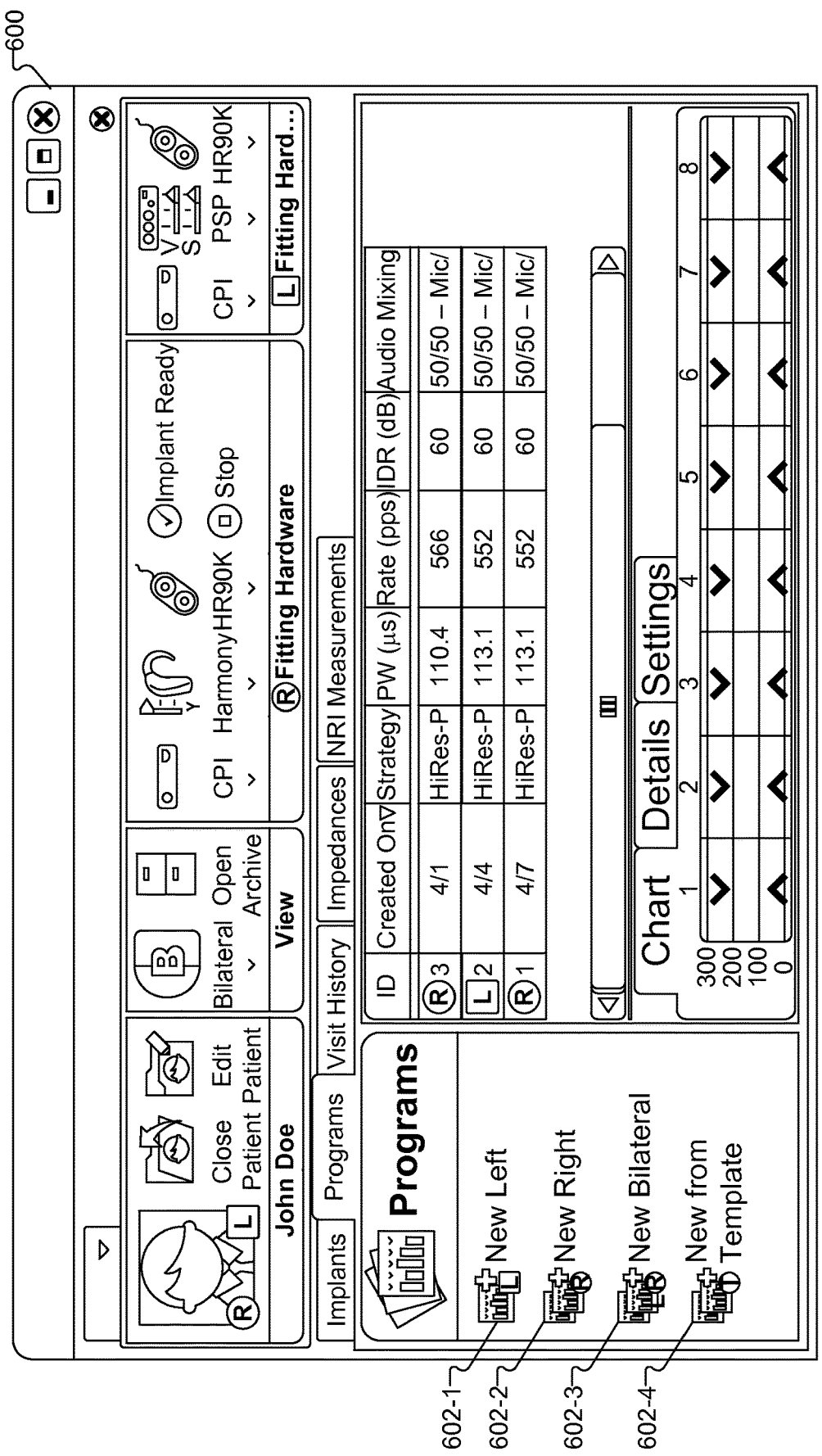
FIGS. 6-12 show various user interface views according to principles described herein.

To illustrate, FIG. 6 illustrates an exemplary user interface 600 that may be presented (e.g., displayed within a display screen) by programming system 302. As shown, user interface 600 includes information descriptive of various sound processing programs that have been created for a particular patient named "John Doe." User interface 600 also includes options 602 (e.g., options 602-1 through 602-4) that may be selected by the user in order to create a new sound processing program. For example, the user may select option 602-1 to create a new sound processing program for a sound processor configured to be used with the patient's left ear, option 602-2 to create a new sound processing program for a sound processor configured to be used with the patient's right ear, option 602-3 to create a new bilateral sound processing program for sound processors configured to be concurrently used with both of the patient's ears or option 602-4 to create a new sound processing program directly from a template.

Returning to FIG. 5, in step 504, programming system 302 provides, in response to the first input command, a user interface that shows a plurality of default values corresponding to a plurality of parameters associated with (i.e., included in) the sound processing program. Step 504 may be performed in any suitable manner.

Figure 7:
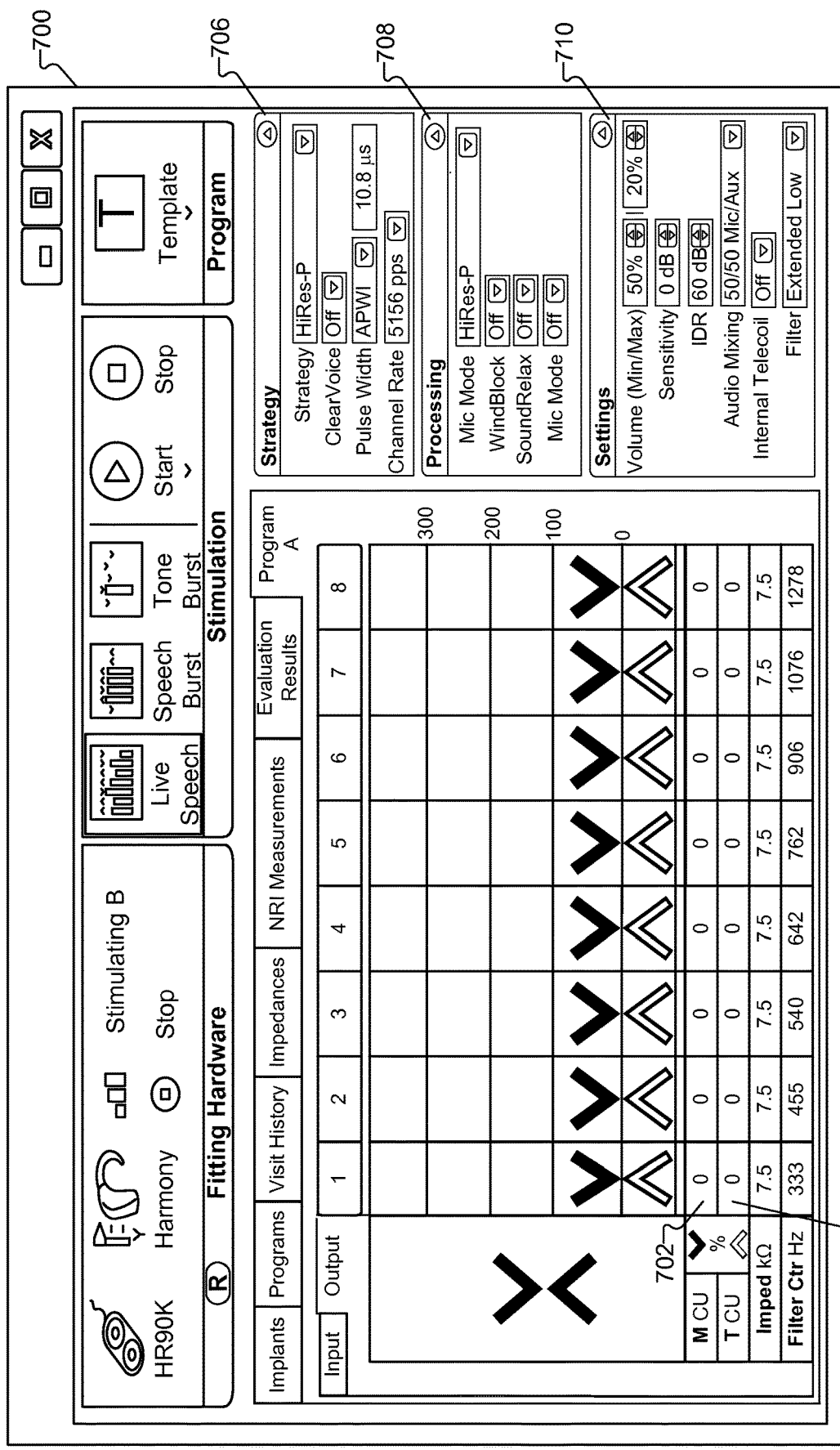

For example, FIG. 7 shows an exemplary user interface 700 that may be provided by programming system 302 in response to a selection by the user of one of options 602 shown in FIG. 6. As shown, user interface 700 shows default values for a plurality of parameters associated with the sound processing program (which is labeled "Program A" in FIG. 7 for illustrative purposes). For example, user interface 700 shows default values for both M and T levels for a group of eight stimulation channels included in the cochlear implant system. To illustrate, field 702 shows that the default value for the M level for a first stimulation channel is 0 CU. Likewise, field 704 shows that the default value for the T level for the first stimulation channel is also 0 CU. User interface 700 also shows default values for various parameters included in a "strategy" category 706, a "processing" category 708, and a "settings" category 710. It will be recognized that default values for additional or alternative parameters associated with the sound processing program may be presented within user interface 700 as may serve a particular implementation.

Returning to FIG. 5, in step 506, programming system 302 detects a changing, by the user by way of the user interface, of the plurality of default values corresponding to the plurality of parameters to a plurality of modified values corresponding to the plurality of parameters. Step 506 may be performed in any suitable manner.

Figure 8:
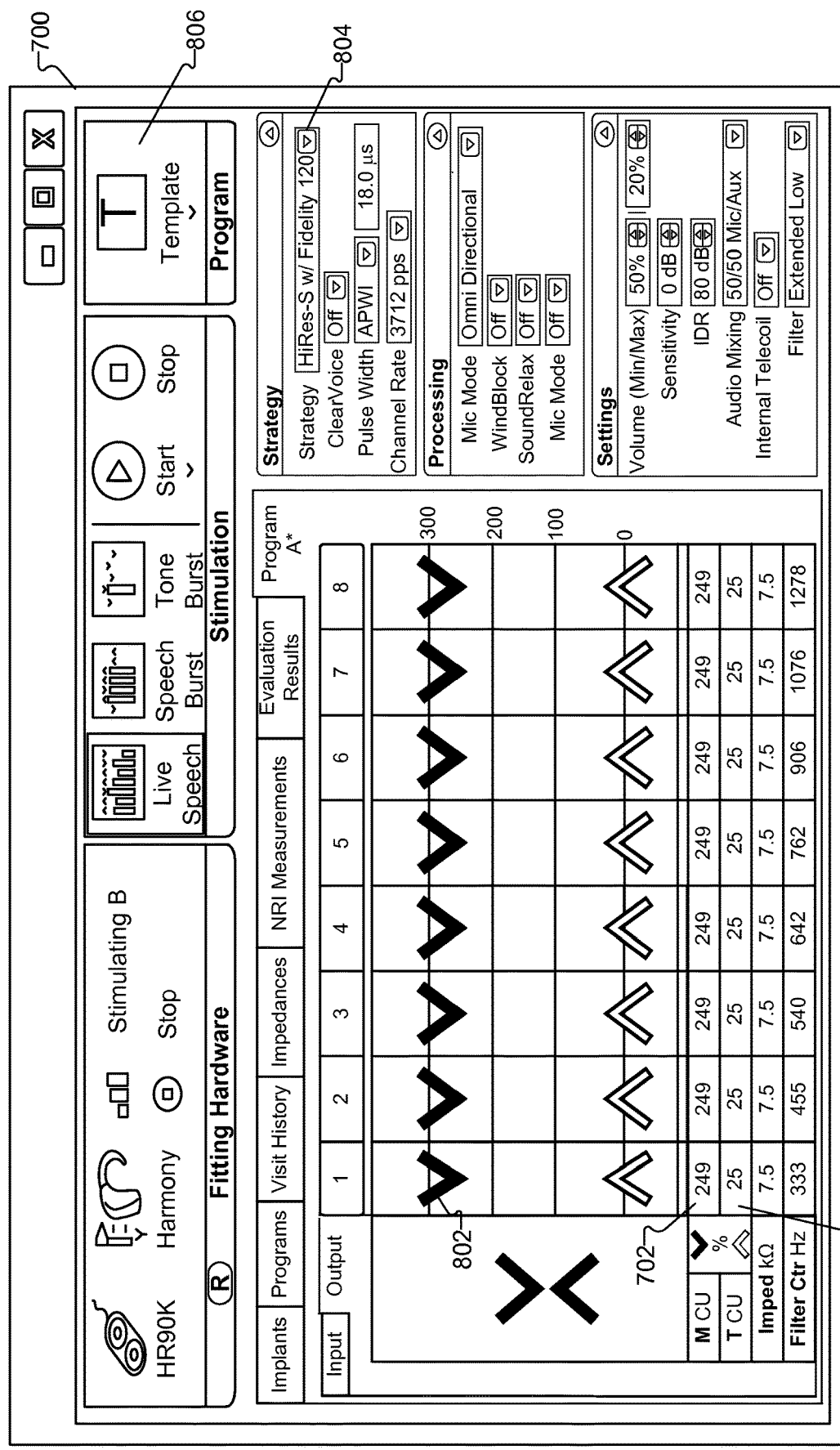

For example, FIG. 8 shows user interface 700 after default values corresponding to some of the parameters associated with the sound processing program have been modified by the user. As shown, the M levels for each of the stimulation channels have been increased by the user from 0 CU to 249 CU. As another example, a "strategy" parameter included in the "strategy" category 706 has been changed from "HiRes-P" to "HiRes-S w/Fidelity 120". Values for various other parameters have also been changed by the user as shown in FIG. 8.

Programming system 302 may facilitate user modification of values presented within user interface in any suitable manner. For example, a user may adjust the M and/or T levels by interacting with (e.g., dragging) one or more graphical objects (e.g., graphical object 802) and/or by inputting desired values directly into one or more fields (e.g., fields 702 and 704). As another example, a user may adjust various values by selecting options from one or more drop down menus (e.g., drop down menu 804).

Returning to FIG. 5, in step 508, programming system 302 detects, subsequent to the changing detected in step 506, a second input command provided by the user and representative of a request to create a sound processing program template configured to serve as a basis for one or more additional sound processing programs. Step 508 may be performed in any suitable manner.

For example, after the user has modified various values shown in the user interface 700 of FIG. 8, the user may select option 806 in order to create a sound processing program template that is based on at least some of the modified values shown in user interface 700 at the time that the user selects option 806.

Returning to FIG. 5, in step 510, programming system 302 presents, in response to the second input command detected in step 508, an option that allows the user to select one or more of the modified values to be included in the sound processing program template. In step 512, programming system 302 detects, while the option is being presented, a selection by the user of one or more modified values included in the plurality of modified values and corresponding to one or more parameters included in the plurality of parameters. Steps 510 and 512 may be performed in any suitable manner.

Figure 9:
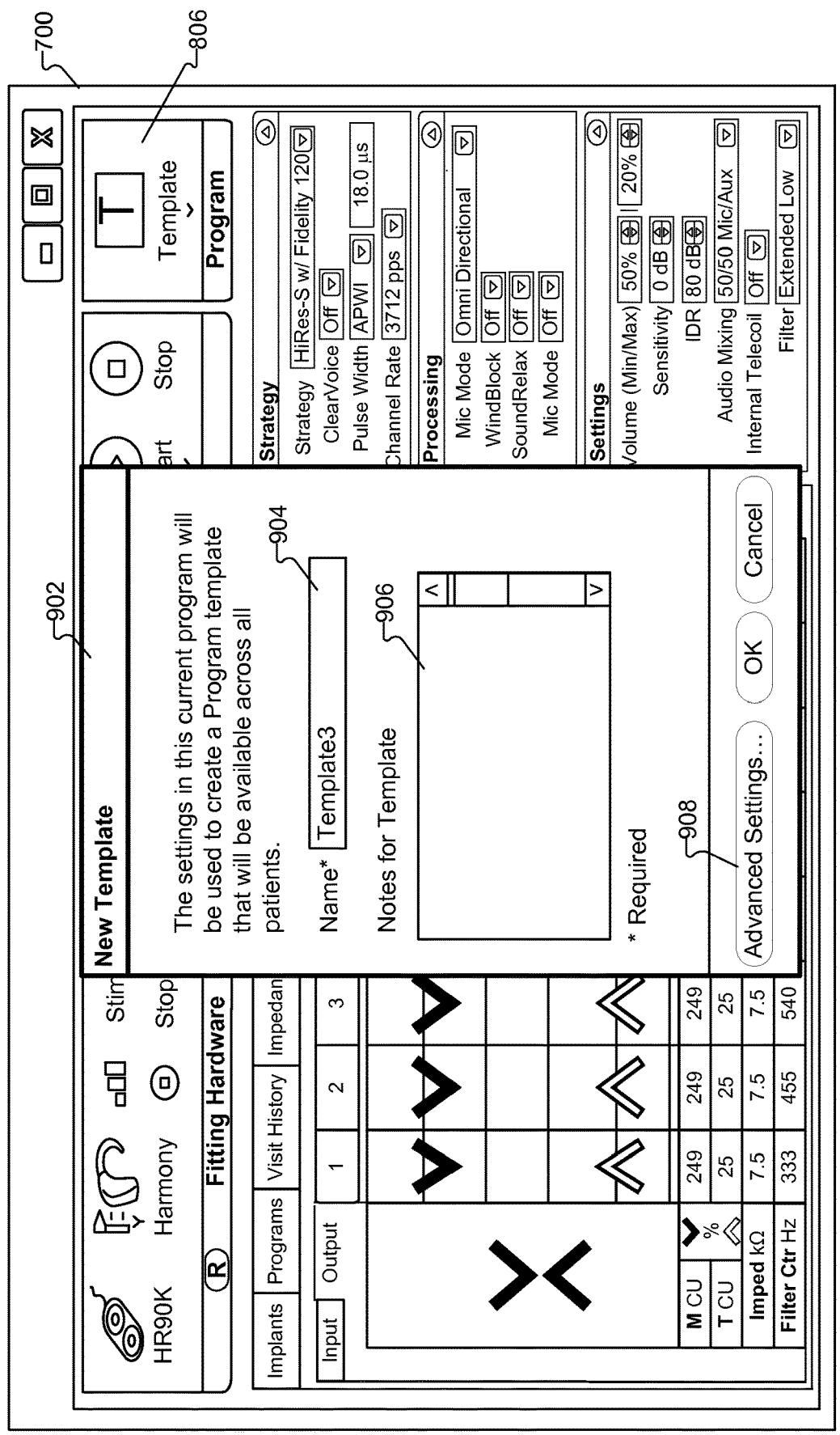

For example, FIG. 9 shows an exemplary manner in which programming system 302 allows the user to select one or more of the modified values to be included in the sound processing program template. As shown in FIG. 9, in response to the user selecting option 806 shown in FIG. 8, programming system 302 may present a user interface 902 (e.g., a pop-up window that is overlaid on top of user interface 700 and/or any other type of user interface as may serve a particular implementation). User interface 902 may include a field 904 in which the user may specify a name of the sound processing program template and a field 906 in which the user may create one or more notes associated with the sound processing program template. For illustrative purposes, the name of the sound processing program template being created in FIG. 9 is "Template3".

Figure 10:
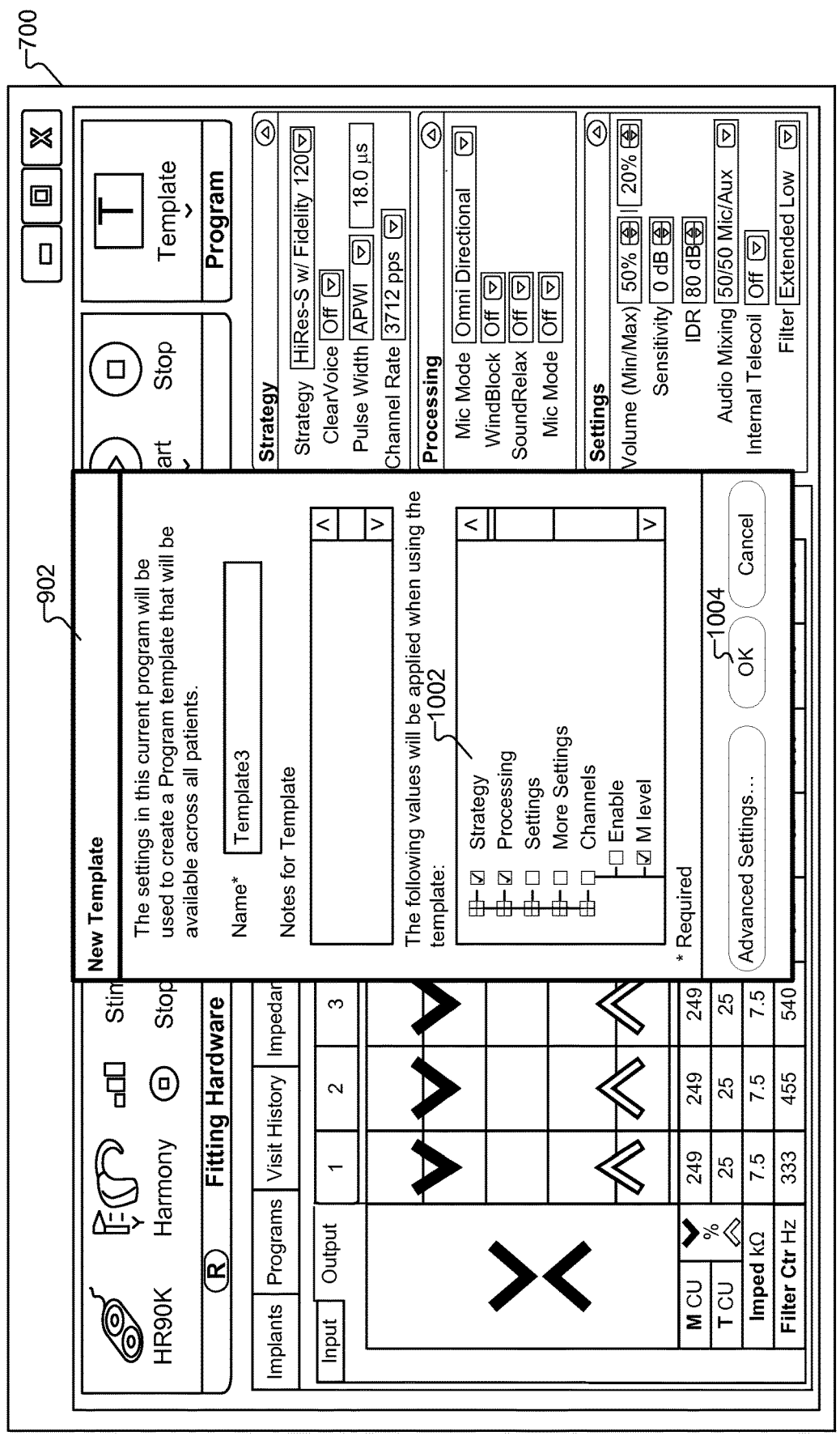

In some examples, user interface 902 may facilitate selection by the user of one or more of the modified values for inclusion in the sound processing program template. To illustrate, FIG. 10 shows that in response to a user selection of option 908, programming system 302 may present a list 1002 of parameters within user interface 902. The user may select one or more of the parameters from list 1002 in order to include their corresponding modified values within the sound processing program template that is to be created.

In some examples, as shown in FIG. 10, list 1002 may be organized into different categories of parameters. In this manner, a user may select a particular category in order to select all of the modified values included within the category for inclusion in the sound processing program template. For example, FIG. 10 shows that the "strategy" and "processing" categories have been selected. Hence, all of the modified values included in categories will be included in the sound processing program template.

Additionally or alternatively, a user may expand a particular category to select individual values within the particular category. For example, FIG. 10 shows that the "channels" category has been expanded, and that the modified values for the M levels have been selected for inclusion in the sound processing program template.

Returning to FIG. 5, in step 514, programming system 302 creates, based on the selection made by the user, the sound processing program template. For example, in response to a user selection of option 1004 shown in FIG. 10, programming system 302 may create the sound processing program template by including the modified values selected within list 1002 in the sound processing program template. In some examples, programming system 302 may exclude modified values that were not selected by user from list 1002 from being included in the sound processing program template. Programming system 302 may instead include default values (which, in some examples, may include one or more "blank" values that have no value) in the sound processing program template for parameters that were not selected by the user. For example, based on the selections made in FIG. 10, programming system 302 may include, within the sound processing program template, the modified values for all parameters included in the "strategy" and "processing" categories and the modified values for the M levels. Programming system 302 may further include default values for the remaining parameters that were not selected by the user (e.g., the parameters included in the "settings" categories).

Once programming system 302 creates the sound processing template, the sound processing template may be used by a user to create a new sound processing program. For example, in some instances, programming system 302 may detect an input command provided by the user and representative of a request to create a new sound processing program based on the sound processing program template. The input command may be provided in any suitable manner. For example, the input command may be provided by selecting an option presented in user interface 600 (e.g., option 602-4).

In response, programming system 302 may create the new sound processing program by including the modified values specified in the sound processing program template in the new sound processing program. The request to create the new sound processing program based on the sound processing program template may be provided by the user in any suitable manner (e.g., by selecting an option presented within any of the user interfaces described herein). Once the new sound processing program has been created using the sound processing program template, programming system 302 may present the values (including the modified values specified in the sound processing program template) for the parameters associated with the new sound processing program in a user interface (e.g., user interface 700) and facilitate further modification of the values by the user.

In some examples, a user may apply a sound processing program template to a sound processing program after the user has already begun modifying the sound processing program. For example, a user may provide an input command representative of a request to create a sound processing program, as described above in FIG. 6. Programming system 302 may detect the input command and, in response, provide user interface 700. As described above, the user may interact with user interface 700 to change various default values associated with the sound processing program. The user may then decide that he or she wants to apply a sound processing program template to the sound processing program. To this end, the user may provide an input command representative of a request to apply the sound processing program template to the sound processing program.

Figure 11:
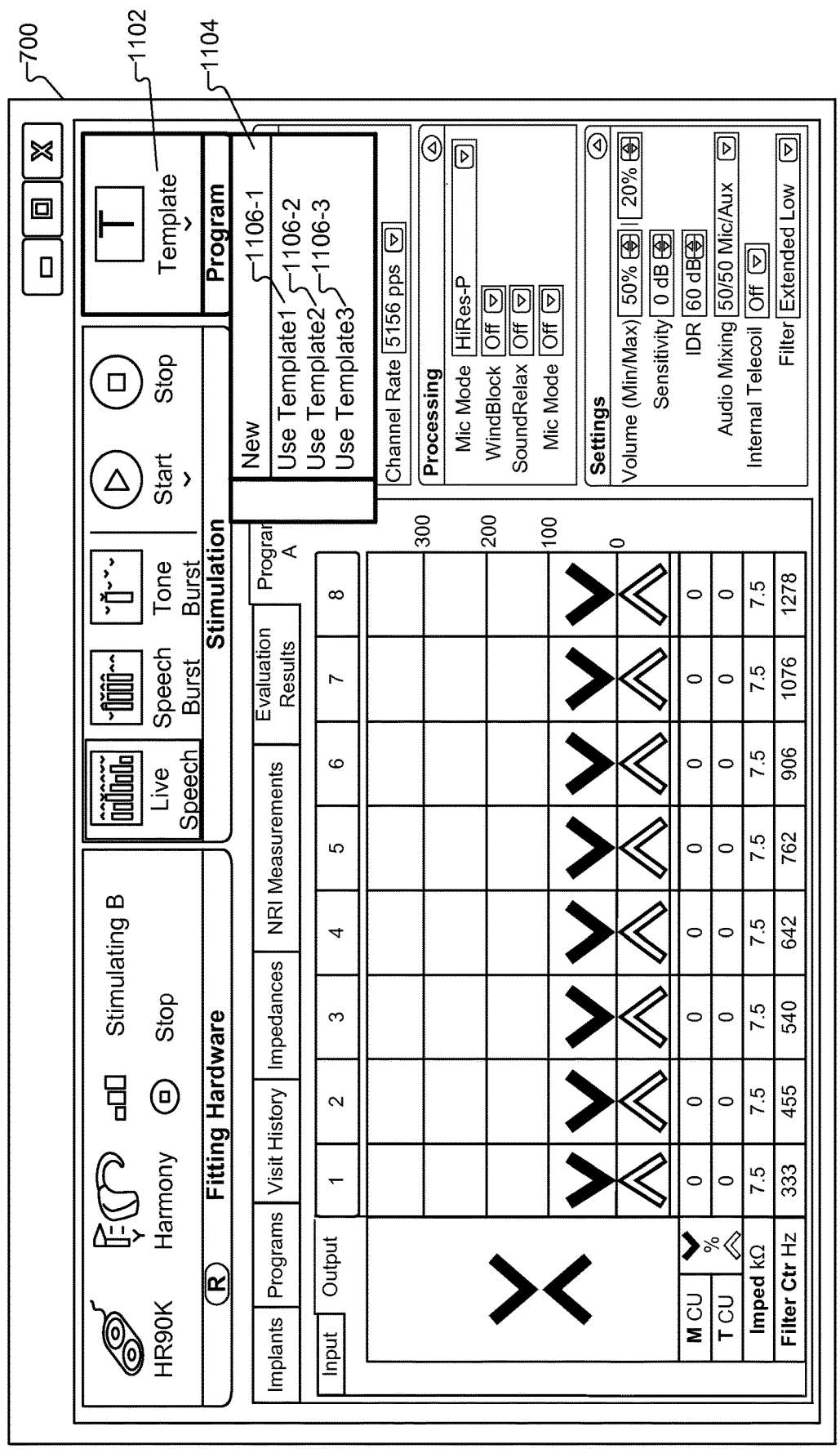

For example, FIG. 11 shows user interface 700 after the user has selected an option 1102 to apply a sound processing program template to the sound processing program being created within user interface 700. As shown, a template menu 1104 has been displayed in response to the selection by the user of option 1102. Template menu 1104 includes entries 1106 (e.g., entries 1106-1 through 1106-3) representative of sound processing program templates that have been created and that are available for use by the user. The user may select an entry from the list in order to apply a desired sound processing program template to the sound processing program that is being created. For example, the user may select entry 1106-3. In response, programming system 302 may apply the sound processing program template entitled "Template3" to the sound processing program being created by overwriting the values presented within user interface 700 with the modified values included in the sound processing program template entitled "Template3".

In some examples, a user may selectively apply only a portion of a sound processing program template to a sound processing program. In other words, the user may choose to only apply some of the modified values included in the sound processing program template to the sound processing program.

Figure 12:
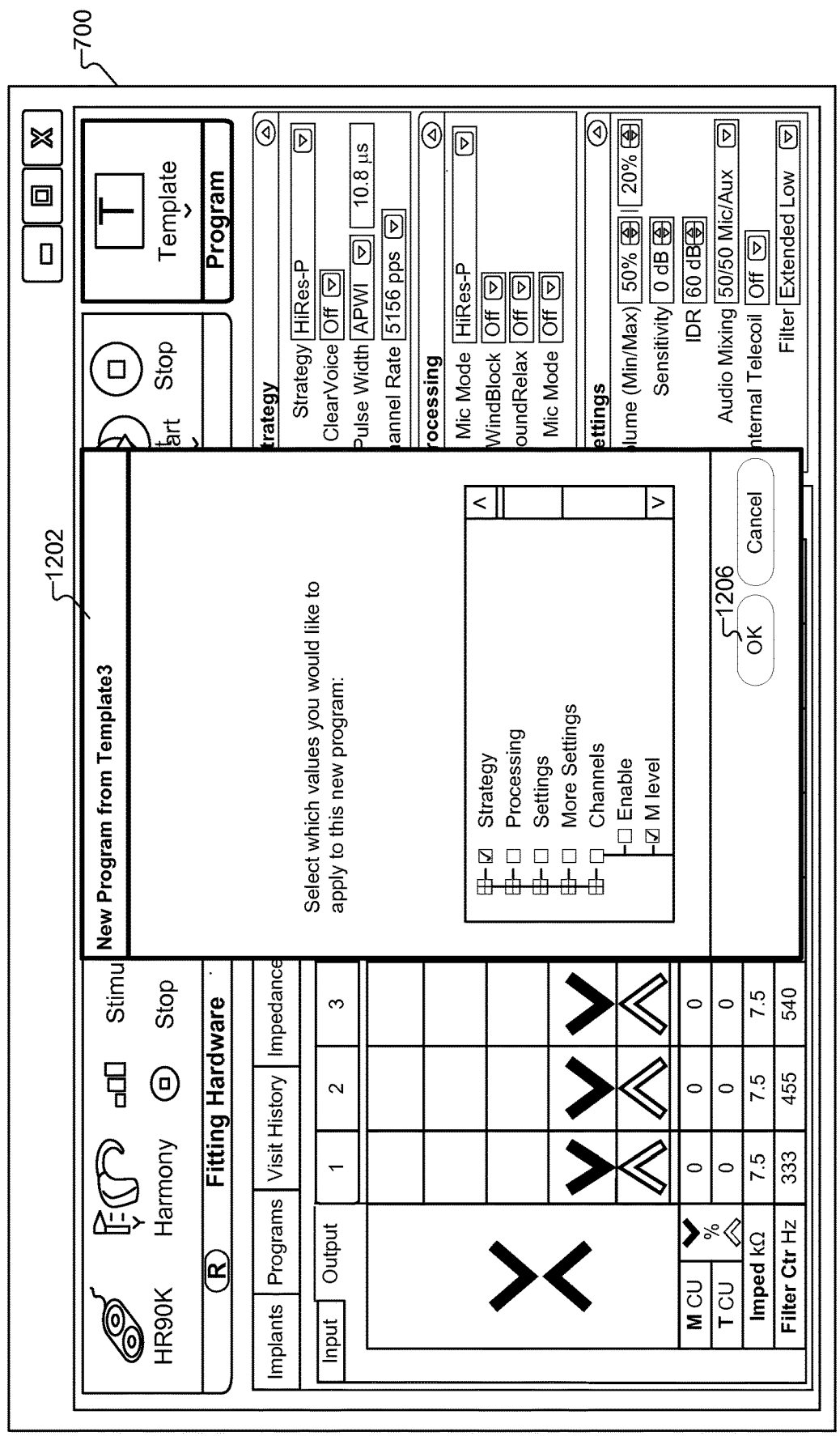

To illustrate, FIG. 12 shows an exemplary option or user interface 1202 (e.g., a pop-up window that is overlaid on top of user interface 700 and/or any other type of user interface as may serve a particular implementation) that may be presented by programming system 302 in response to the user selecting entry 1106-3 in FIG. 11. As shown, user interface 1202 may allow the user to select one or more modified values included in the sound processing program template for application to the sound processing program. To illustrate, FIG. 12 shows that the user has selected the "strategy" category and the "M level" within user interface 1202. Hence, if the user selects option 1206, programming system 302 will create a new sound processing program that includes the modified values for each parameter included in the "strategy" category and for the M levels parameters as specified in the sound processing program template. Programming system 302 will include default values for the remaining unselected parameters.

In some examples, programming system 302 may apply the selected modified values to the new sound processing program in a manner that ensures that the sound processing program does not enter into an invalid state. For example, certain parameters may be dependent on or restricted by other parameters. Hence, programming system 302 may apply modified values for the parameters in an order that minimizes conflict. In some examples, if a conflict arises, programming system 302 may alert the user so that the user may take appropriate remedial action.

In some examples, a sound processing program template may be used to create a sound processing program for the same cochlear implant system that was connected to programming system 302 when the sound processing program template was created. Additionally or alternatively, the sound processing program template may be used to create a sound processing program for a different cochlear implant system than the cochlear implant system that was connected to programming system 302 when the sound processing program template was created.

It will be recognized that any sound processing program template created prior to programming system 302 detecting an input command to create a new sound processing program may be used to create the new sound processing program. For example, a sound processing program template may be created by a system other than programming system 302 and then shared with or otherwise provided to programming system 302.

To illustrate, a first clinician may utilize a first programming system to create a sound processing program template. The first clinician may export the sound processing program template from the sound processing program template (e.g., by exporting the sound processing program template to an electronic file). The exported sound processing program template may then be shared (e.g., transmitted to) a second programming system used by a second clinician. The second clinician may import the exported sound processing program template and thereby use the sound processing program template to create a sound processing program for a different patient.

As another example, programming system 302 may be provided with a "pre-packaged" sound processing program template, which may then be used to create a new sound processing program. The pre-packaged sound processing program template may be created, for example, by a provider of programming system 302, a provider (e.g., a manufacturer) of a sound processor and/or a cochlear implant, and/or any other entity as may serve a particular implementation. The pre-packaged sound processing program template may be provided to programming system 302 by an entity (e.g., a system, a person, etc.) other than the programming system 302 in any suitable manner. For example, the pre-packaged sound processing program template may be included in a software package utilized by programming system 302, imported into programming system 302 from a file, etc.

In some examples, a pre-packaged sound processing template may include one or more values that have already been modified compared to their respective default values.

For example, a pre-packaged sound processing template may include one or more values that have been modified in a manner that suits an NRI procedure performed on a sedated patient in an operating room. In this scenario, the pre-packaged sound processing template may specify relatively loud stimulation levels (e.g., levels higher than default values and that would generally be uncomfortable for a patient not under sedation). In this manner, a user may use the pre-packaged sound processing template to more efficiently and effectively create a sound processing program configured to facilitate NRI for a particular patient. In a similar manner, different pre-packaged sound processing templates may be provided and used to create sound processing programs for pediatric patients versus adult patients, bilateral configurations versus single-sided configurations, etc.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 13:
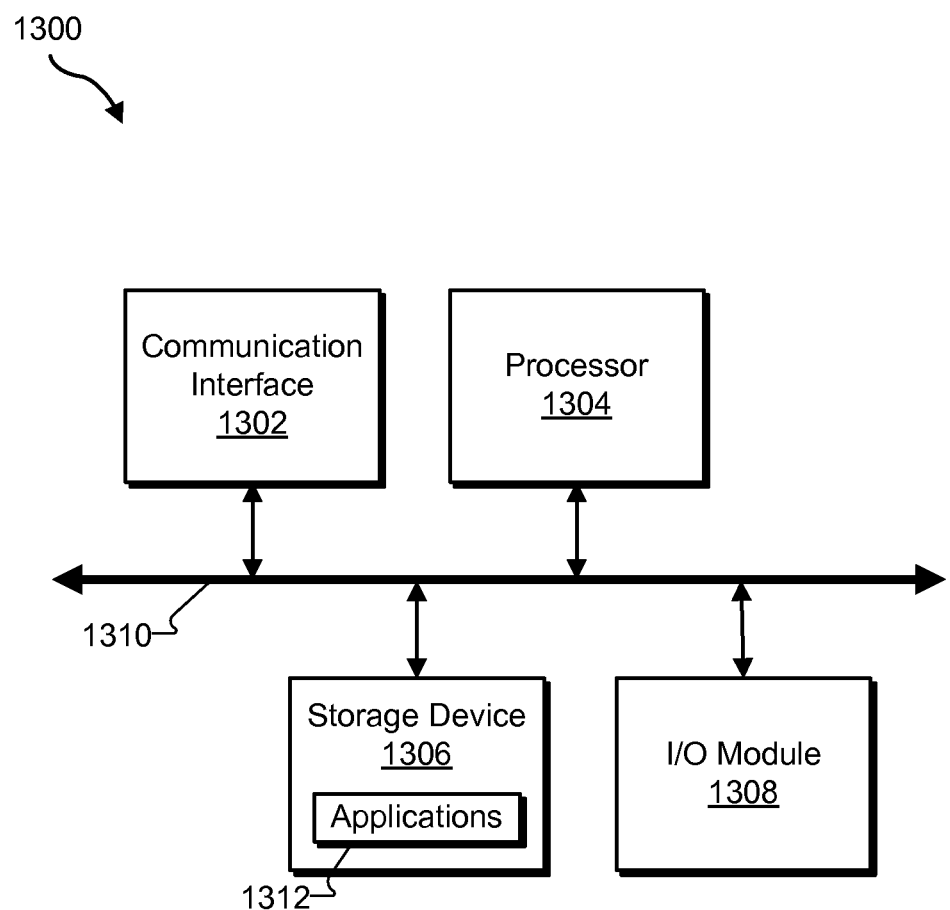
FIG. 13 illustrates an exemplary computing device according to principles described herein.

FIG. 13 illustrates an exemplary computing device 1300 that may be specifically configured to perform one or more of the processes described herein. As shown in FIG. 13, computing device 1300 may include a communication interface 1302, a processor 1304, a storage device 1306, and an input/output ("I/O") module 1308 communicatively connected via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data or interpreting, executing, and/or directing execution of one or more of the instructions, processes, and/or operations described herein. Processor 1304 may direct execution of operations in accordance with one or more applications 1312 or other computer-executable instructions such as may be stored in storage device 1306 or another computer-readable medium.

Storage device 1306 may include one or more data storage media, devices, or configurations and may employ any type, form, and combination of data storage media and/or device. For example, storage device 1306 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1306. For example, data representative of one or more executable applications 1312 configured to direct processor 1304 to perform any of the operations described herein may be stored within storage device 1306. In some examples, data may be arranged in one or more databases residing within storage device 1306.

I/O module 1308 may be configured to receive user input and provide user output and may include any hardware, firmware, software, or combination thereof supportive of input and output capabilities. For example, I/O module 1308 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1300. For example, one or more applications 1312 residing within storage device 1306 may be configured to direct processor 1304 to perform one or more processes or functions associated with management facility 402. Likewise, storage facility 404 may be implemented by or within storage device 1306.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to
detect a first input command provided by a user and representative of a request to create a sound processing program;
provide, in response to the first input command, a first user interface that shows a plurality of default values corresponding to a plurality of parameters associated with the sound processing program;
detect a changing, by the user by way of the first user interface, of the plurality of default values corresponding to the plurality of parameters to a plurality of modified values corresponding to the plurality of parameters;
detect, subsequent to the changing, a second input command provided by the user and representative of a request to create a sound processing program template configured to serve as a basis for one or more additional sound processing programs;
present, in response to the second input command, a second user interface that includes a list of the plurality of parameters;
detect a selection by the user of one or more parameters included in the list presented in the second user interface; and
create the sound processing program template by including, in the sound processing program template,
modified values included in the plurality of modified values and corresponding to the one or more parameters selected by the user, and
default values included in the plurality of default values and corresponding to a remaining number of parameters not selected by the user from the list.

2. The system of claim 1, wherein the processor is further configured to execute the instructions to:
detect, subsequent to the creation of the sound processing program template, a third input command provided by the user and representative of a request to create an additional sound processing program based on the sound processing program template; and
create, in response to the third input command, the additional sound processing program by including the one or more modified values for the one or more parameters in the additional sound processing program.

3. The system of claim 2, wherein the processor is further configured to execute the instructions to:
present, within the first user interface, the one or more modified values for the one or more parameters and the default values included in the plurality of default values for the remaining number of parameters included in the plurality of parameters but not included in the one or more parameters; and
facilitate further modification, by the user by way of the first user interface, of any of the values presented within the first user interface.

4. The system of claim 2, wherein the processor is further configured to execute the instructions to load the additional sound processing program onto a sound processor included in a cochlear implant system.

5. The system of claim 1, wherein the sound processing program is for a cochlear implant system.

6. The system of claim 5, wherein the additional sound processing program is created for an additional cochlear implant system that is different from the cochlear implant system.

7. The system of claim 5, wherein the additional sound processing program is created for the cochlear implant system.

8. The system of claim 1, wherein the processor is further configured to execute the instructions to:
detect, subsequent to the creation of the sound processing program template, a third input command provided by the user and representative of a request to create an additional sound processing program;
provide, in response to the third input command, an additional user interface that shows the plurality of default values corresponding to the plurality of parameters, the plurality of parameters also corresponding to the additional sound processing program;
detect a changing, by the user by way of the additional user interface, of a default value included in the plurality of default values;
detect, subsequent to the changing of the default value, a fourth input command provided by the user and representative of a request to apply the sound processing program template to the additional sound processing program; and
apply, in response to the fourth input command, the sound processing program template to the additional sound processing program by overwriting one or more of the default values with one or more of the one or more modified values included in the sound processing program template.

9. The system of claim 1, wherein the processor is further configured to execute the instructions to:
detect, subsequent to the creation of the sound processing program template, a third input command provided by the user and representative of a request to create an additional sound processing program based on the sound processing program template;
present, in response to the third input command, an option that allows the user to select one or more of the one or more modified values included in the sound processing program template to be used for the additional sound processing program;
detect, while the option is being presented, a selection by the user of a particular modified value included in the one or more modified values and corresponding to a particular parameter included in the plurality of parameters; and
create, subsequent to the selection of the particular modified value, the additional sound processing program by including, in the additional sound processing program, the particular modified value for the particular parameter and default values included in the plurality of default values for a remaining number of parameters included in the plurality of parameters.

10. The system of claim 1, wherein:
the list is organized into a plurality of categories; and the detecting of the selection by the user of the one or more parameters comprises detecting a selection of a particular category included in the plurality of categories.

11. The system of claim 1, wherein the second user interface comprises a pop-up window that is overlaid on top of the first user interface.

12. A system comprising:
a memory storing instructions; and
a processor communicatively coupled to the memory and configured to execute the instructions to
  detect an input command provided by a user and representative of a request to create a sound processing program that is based on a sound processing program template created prior to the input command being provided, wherein the sound processing program template includes a plurality of modified values corresponding to a plurality of parameters associated with the sound processing program, the modified values being modified with respect to a plurality of default values corresponding to the plurality of parameters;
  present, in response to the input command, a user interface that includes a list of the plurality of parameters;
  detect, while the user interface is being presented, a selection by the user of a particular parameter included in the plurality of parameters included in the list and having a particular modified value; and
  create, subsequent to the selection of the particular parameter, the sound processing program by including, in the sound processing program, the particular modified value for the particular parameter and default values included in the plurality of default values for a remaining number of parameters included in the list that are not selected by the user, wherein the default values are different from the modified values.

13. The system of claim 12, wherein the processor is further configured to execute the instructions to load the sound processing program onto a sound processor included in a cochlear implant system.

14. The system of claim 12, wherein the sound processing program template is a pre-packaged sound processing program template provided to the system.

15. The system of claim 14, wherein the pre-packaged sound processing program template specifies relatively loud stimulation levels for use during a neural response imaging procedure performed on a sedated patient in an operating room.

16. A method comprising:
  detecting, by a programming system, a first input command provided by a user and representative of a request to create a sound processing program;
  providing, by the programming system in response to the first input command, a first user interface that shows a plurality of default values corresponding to a plurality of parameters associated with the sound processing program;
  detecting, by the programming system, a changing, by the user by way of the first user interface, of the plurality of default values corresponding to the plurality of parameters to a plurality of modified values corresponding to the plurality of parameters;
  detecting, by the programming system subsequent to the changing, a second input command provided by the user and representative of a request to create a sound processing program template configured to serve as a basis for one or more additional sound processing programs;
  presenting, by the programming system in response to the second input command, a second user interface that includes a list of the plurality of parameters;
  detecting, by the programming system, a selection by the user of one or more parameters included in the list presented in the second user interface; and
  creating, by the programming system, the sound processing program template by including, in the sound processing program template,
    modified values included in the plurality of modified values and corresponding to the one or more parameters selected by the user, and
    default values included in the plurality of default values and corresponding to a remaining number of parameters not selected by the user from the list.

17. The method of claim 16, further comprising:
  detecting, by the programming system subsequent to the creation of the sound processing program template, a third input command provided by the user and representative of a request to create an additional sound processing program based on the sound processing program template; and
  creating, by the programming system in response to the third input command, the additional sound processing program by including the one or more modified values for the one or more parameters in the additional sound processing program.

18. The method of claim 17, further comprising loading, by the programming system, the additional sound processing program onto a sound processor included in a cochlear implant system.

19. The method of claim 16, further comprising:
  detecting, by the programming system subsequent to the creation of the sound processing program template, a third input command provided by the user and representative of a request to create an additional sound processing program;
  providing, by the programming system in response to the third input command, an additional user interface that shows the plurality of default values corresponding to the plurality of parameters, the plurality of parameters also corresponding to the additional sound processing program;
  detecting, by the programming system, a changing, by the user by way of the additional user interface, of a default value included in the plurality of default values;
  detecting, by the programming system subsequent to the changing of the default value, a fourth input command provided by the user and representative of a request to apply the sound processing program template to the additional sound processing program; and
  applying, by the programming system in response to the fourth input command, the sound processing program template to the additional sound processing program by overwriting one or more of the default values with one or more of the one or more modified values included in the sound processing program template.

20. The method of claim 16, wherein the sound processing program is for a cochlear implant system.

* * * * *